US008852284B2

(12) United States Patent
Wiley et al.

(10) Patent No.: US 8,852,284 B2

(45) Date of Patent: Oct. 7, 2014

(54) HYDROGEL PROXIMAL INTERPHALANGEAL IMPLANT

(75) Inventors: Roy C. Wiley, Warsaw, IN (US); Antony J. Lozier, Warsaw, IN (US); Mary Phillips, Bay City, MI (US)

(73) Assignee: Zimmer, Inc., Warsaw, IN (US)

( * ) Notice: Subject to any disclaimer, the term of this patent is extended or adjusted under 35 U.S.C. 154(b) by 757 days.

(21) Appl. No.: 12/025,959

(22) Filed: Feb. 5, 2008

(65) Prior Publication Data

US 2008/0195219 A1 Aug. 14, 2008

Related U.S. Application Data

(60) Provisional application No. 60/888,841, filed on Feb. 8, 2007.

(51) Int. Cl.
*A61F 2/38* (2006.01)

(52) U.S. Cl.
USPC .................. 623/20.15; 623/20.16; 623/20.17

(58) Field of Classification Search
None
See application file for complete search history.

(56) References Cited

U.S. PATENT DOCUMENTS 3,593,342 A * 7/1971 Niebauer et al. ........... 623/23.41
3,875,594 A 4/1975 Swanson
3,886,600 A * 6/1975 Kahn et al. ................. 623/20.24
4,313,232 A 2/1982 Habal et al.
4,502,161 A 3/1985 Wall
4,839,215 A 6/1989 Starling et al.
4,966,924 A 10/1990 Hyon et al.
5,041,138 A 8/1991 Vacanti et al.
5,147,904 A 9/1992 Jochum et al.
5,282,861 A 2/1994 Kaplan
5,314,478 A 5/1994 Oka et al.
5,358,525 A 10/1994 Fox et al.
5,458,643 A 10/1995 Oka et al.
5,556,429 A 9/1996 Felt
5,607,474 A 3/1997 Athanasiou et al.
5,645,592 A 7/1997 Nicolais et al.
5,658,343 A 8/1997 Hauselmann et al.
5,699,657 A 12/1997 Paulson
5,728,157 A 3/1998 Prescott
5,795,353 A 8/1998 Felt
6,077,989 A 6/2000 Kandel et al.

(Continued)

FOREIGN PATENT DOCUMENTS

DE 2933174 A1 4/1980
DE 19721661 A1 11/1998

(Continued)

OTHER PUBLICATIONS

Product Brochure—Ascension Silicone MCP, Ascension Orthopedics, Inc. 2004.

(Continued)

*Primary Examiner* — David Isabella
*Assistant Examiner* — Joshua Levine
(74) *Attorney, Agent, or Firm* — Schwegman Lundberg & Woessner, P.A.

(57) ABSTRACT

A prosthetic for use in an interphalangeal joint including a body portion and a weave portion. The body portion may be manufactured from a hydrogel material. The body portion includes an pair of stems and an intermediate section located in between the two stems. The intermediate section includes a recess allowing for flexing of the body portion.

15 Claims, 3 Drawing Sheets

2
4
6
7
9

(56) References Cited

U.S. PATENT DOCUMENTS

| | | | | |
|---|---|---|---|---|
| 6,132,468 | A | 10/2000 | Mansmann | |
| 6,140,452 | A | 10/2000 | Felt et al. | |
| 6,224,630 | B1 | 5/2001 | Bao et al. | |
| 6,231,605 | B1 | 5/2001 | Ku | |
| 6,306,177 | B1 | 10/2001 | Felt et al. | |
| 6,425,923 | B1 | 7/2002 | Stalcup et al. | |
| 6,443,988 | B2 | 9/2002 | Felt et al. | |
| 6,447,514 | B1 | 9/2002 | Stalcup et al. | |
| 6,468,314 | B2 | 10/2002 | Schwartz et al. | |
| 6,494,917 | B1 | 12/2002 | McKellop et al. | |
| 6,530,956 | B1 | 3/2003 | Mansmann | |
| 6,533,818 | B1 | 3/2003 | Weber et al. | |
| 6,547,828 | B2 | 4/2003 | Scott et al. | |
| 6,562,073 | B2 | 5/2003 | Foley | |
| 6,620,196 | B1 | 9/2003 | Trieu | |
| 6,629,997 | B2 | 10/2003 | Mansmann | |
| 6,679,913 | B2 | 1/2004 | Homsy | |
| 6,719,797 | B1 | 4/2004 | Ferree | |
| 6,827,743 | B2 | 12/2004 | Eisermann | |
| 6,869,449 | B2 | 3/2005 | Ball et al. | |
| 6,994,730 | B2 | 2/2006 | Posner | |
| 7,001,431 | B2 | 2/2006 | Bao et al. | |
| 7,077,865 | B2 | 7/2006 | Bao et al. | |
| 7,083,648 | B2 | 8/2006 | Yu et al. | |
| 7,291,169 | B2 | 11/2007 | Hodorek | |
| 2001/0033857 | A1 | 10/2001 | Vyakarnam et al. | |
| 2001/0039455 | A1 | 11/2001 | Simon et al. | |
| 2001/0046518 | A1* | 11/2001 | Sawhney | 424/486 |
| 2002/0022884 | A1 | 2/2002 | Mansmann | |
| 2002/0029083 | A1 | 3/2002 | Zucherman et al. | |
| 2002/0156531 | A1 | 10/2002 | Felt et al. | |
| 2002/0173855 | A1 | 11/2002 | Mansmann | |
| 2002/0183845 | A1 | 12/2002 | Mansmann | |
| 2002/0193883 | A1 | 12/2002 | Wironen | |
| 2003/0008396 | A1 | 1/2003 | Ku | |
| 2003/0074076 | A1 | 4/2003 | Ferree et al. | |
| 2003/0078617 | A1 | 4/2003 | Schwartz et al. | |
| 2003/0195628 | A1 | 10/2003 | Bao et al. | |
| 2003/0220649 | A1 | 11/2003 | Bao et al. | |
| 2004/0010312 | A1 | 1/2004 | Enayati | |
| 2004/0039447 | A1 | 2/2004 | Simon et al. | |
| 2004/0051213 | A1 | 3/2004 | Muratoglu | |
| 2004/0070107 | A1 | 4/2004 | Stoy | |
| 2004/0133275 | A1 | 7/2004 | Mansmann | |
| 2004/0138754 | A1 | 7/2004 | Lang et al. | |
| 2004/0153163 | A1 | 8/2004 | Posner | |
| 2004/0163681 | A1 | 8/2004 | Verhaverbeke | |
| 2004/0199250 | A1 | 10/2004 | Fell | |
| 2004/0236424 | A1 | 11/2004 | Berez et al. | |
| 2005/0043808 | A1 | 2/2005 | Felt et al. | |
| 2005/0125077 | A1 | 6/2005 | Harmon et al. | |
| 2005/0171604 | A1 | 8/2005 | Michalow | |
| 2005/0251149 | A1 | 11/2005 | Wenz | |
| 2005/0251266 | A1 | 11/2005 | Maspero et al. | |
| 2005/0251268 | A1 | 11/2005 | Truncale | |
| 2005/0287187 | A1* | 12/2005 | Mansmann | 424/423 |
| 2006/0009853 | A1 | 1/2006 | Justin et al. | |
| 2006/0052878 | A1* | 3/2006 | Schmieding | 623/23.4 |
| 2006/0079905 | A1 | 4/2006 | Bayar et al. | |
| 2006/0224244 | A1 | 10/2006 | Thomas et al. | |
| 2006/0235542 | A1 | 10/2006 | Hodorek et al. | |
| 2006/0253200 | A1 | 11/2006 | Bao et al. | |
| 2007/0027230 | A1 | 2/2007 | Beyar et al. | |
| 2007/0038300 | A1 | 2/2007 | Bao et al. | |
| 2007/0088444 | A1 | 4/2007 | Hodorek et al. | |
| 2007/0142916 | A1 | 6/2007 | Olson et al. | |
| 2007/0179607 | A1 | 8/2007 | Hodorek et al. | |
| 2007/0224238 | A1 | 9/2007 | Mansmann et al. | |
| 2008/0051889 | A1 | 2/2008 | Hodorek | |
| 2008/0125863 | A1 | 5/2008 | McKay | |

FOREIGN PATENT DOCUMENTS

| | | | |
|---|---|---|---|
| DE | 20303205 | U1 | 4/2003 |
| DE | 10220368 | A1 | 12/2003 |
| EP | 0528080 | A1 | 2/1993 |
| GB | 1479693 | | 7/1977 |
| WO | WO 2005/051242 | A1 | 6/2005 |
| WO | WO 2006/060555 | A1 | 6/2006 |

OTHER PUBLICATIONS

Surgical Technique—Ascension PIP PyroCarbon Total Joint, Ascension Orthopedics, Inc., 2005.

Patient Information—Ascension PIP PyroCarbon Total Joint, Ascension Orthopedics, Inc., Jan. 2003.

Website—www.jointreplacement.com—NeuFlex MCP/PIP Finger Joint Implant Systems for Finger Joint Replacement Surgery, DePuy Orthopaedics, Inc. 2000-2006.

Copy of the European Search Report mailed Jun. 23, 2008, in related European Application No. 08250443.2.

Quinton, J.S. and P.C. Dastoor, "Characterizing the bonding mechanisms at silane-metal interfaces: A model system," J. Mat. Sci. Letters. vol. 18, Nov. 1999, pp. 1833-1835 (Quinton).

"Canadian Application Serial No. 2,618,125, Voluntary Amendment filed Feb. 4, 2013", 2 pgs.

* cited by examiner

HYDROGEL PROXIMAL INTERPHALANGEAL IMPLANT

CROSS-REFERENCE TO RELATED APPLICATIONS

The present application claims priority to U.S. Provisional Patent Application Ser. No. 60/888,841, filed Feb. 8, 2007, the entire disclosure of which is incorporated by reference herein.

BACKGROUND

1. Field of the Invention

The present invention relates to the field of joint replacement. Specifically, the present invention relates to a joint prosthesis for proximal interphalangeal joints.

2. Description of the Related Art

The replacement of damaged or diseased joints in the human body has been known for some time. Devices utilized to replace natural joint structures generally mimic natural movement of the joint. In addition, such devices are often configured to provide for a natural "at rest" position similar to that of the natural joint.

Known proximal interphalangeal joint prosthetics typically employ two stems or arms with an intermediate pivoting structure. In some devices, the entire prosthetic is manufactured from a single elastomer material or from metal alloy.

SUMMARY

The present invention relates to a prosthetic used to replace a damaged joint, such as a pivotal interphalangeal joint, for example. The prosthetic may include a body portion and an outer weave portion. The body portion may include an intermediate portion and a pair of stems connected to, and extending from, the intermediate portion.

The body portion may be formed from a hydrogel material, which may expand upon absorption of water. In addition, the outer weave portion may include a plurality of layers including a polymer layer and a metal layer. The polymer layer may be located intermediate the metal layer.

The intermediate portion may include a recess, which may be formed in the palmar side of the intermediate portion.

In one form thereof, the present invention provides a prosthetic used to replace a damaged joint including a body portion including an intermediate portion and a pair of stems connected to the intermediate portion; and an outer weave encompassing the body portion.

In another form, the present invention provides a prosthetic used to replace a damaged joint including a body portion including an intermediate portion and a pair of stems connected to the intermediate portion; wherein the body portion is formed from hydrogel.

In another form, the present invention provides a prosthetic used to replace a damaged joint including a body portion formed from a hydrogel material and including a pair of interconnected stems; and an outer weave at least partially encompassing at least one of the stems.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION

Figure 1:
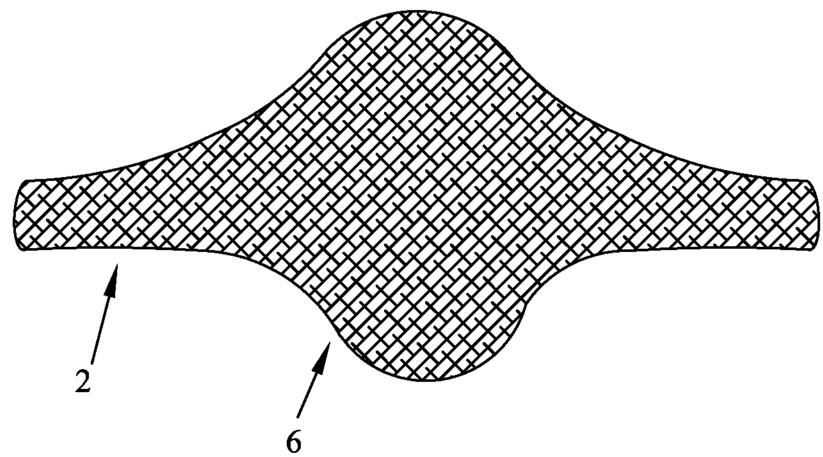
FIG. 1 is a perspective view of a prosthetic device embodying the present invention.
Figure 2:
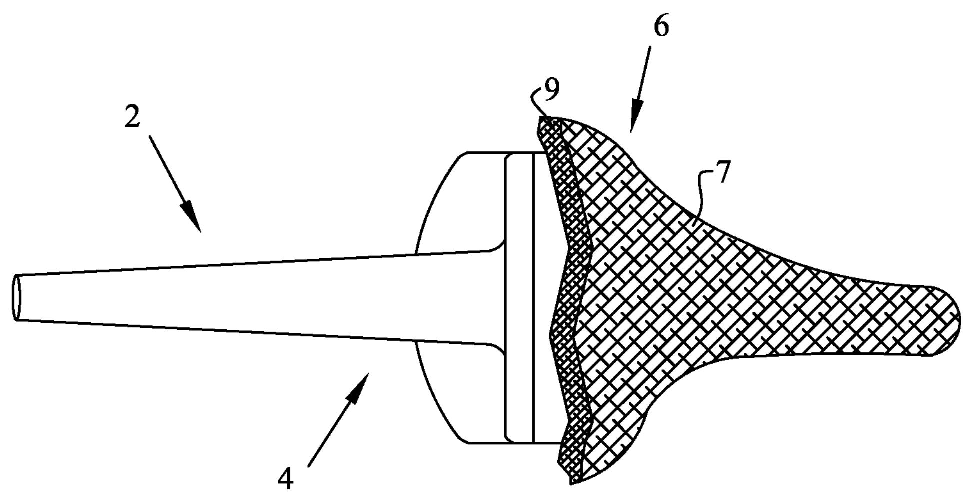
FIG. 2 is a perspective view of the prosthetic device of FIG. 1 with a portion of the outer weave omitted for illustrative purposes.
Figure 7:
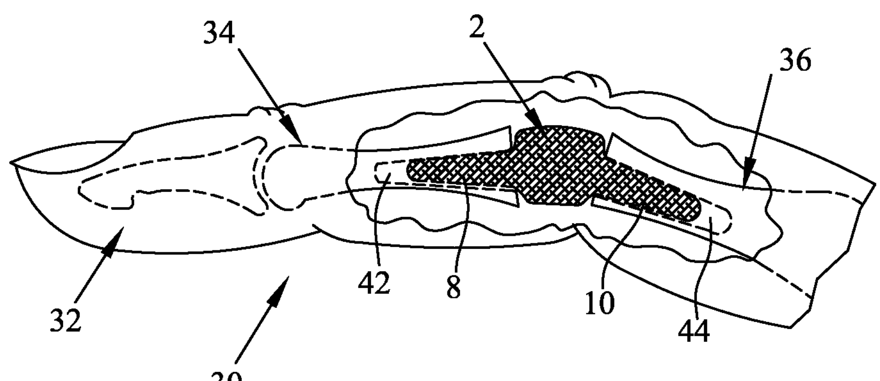

FIGS. 1 and 2 depict different views of a joint prosthetic, generally indicated by numeral 2, representing an exemplary embodiment of the present invention. Prosthetic 2 includes a body portion 4 and a cover or weave portion 6 encompassing body portion 4. In FIG. 2, a portion of weave portion 6 has been omitted in order to illustrate body portion 4 with respect to weave portion 6. The depicted embodiment of prosthetic 2 is configured to be utilized in the proximal interphalangeal (PIP) joint of a human finger 30, as shown in FIG. 7.

Figure 3:
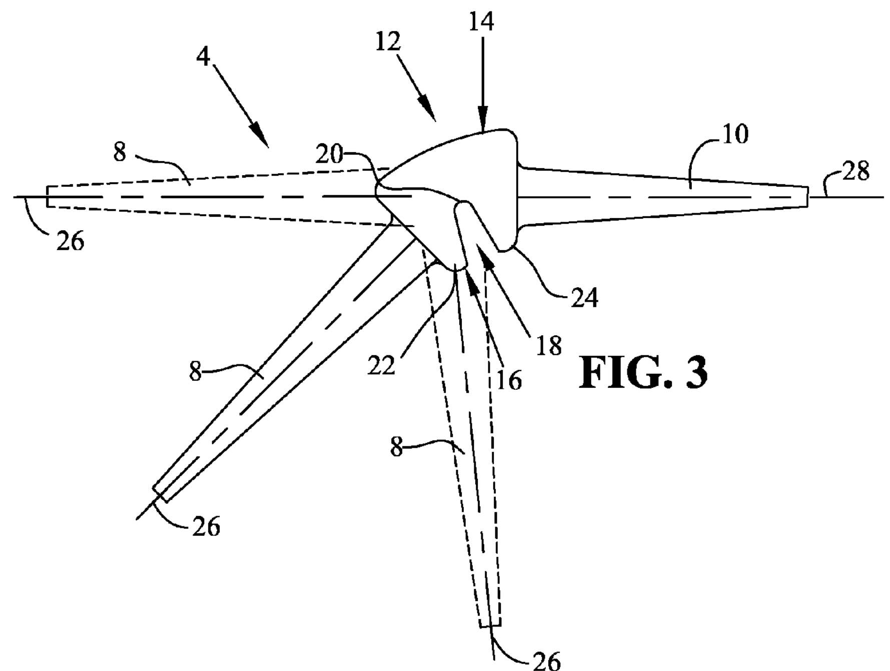
FIG. 3 is a side view of a body portion of the prosthetic device, illustrating exemplary ranges of motion thereof from a substantially non-flexed or neutral position shown in solid lines.
Figure 4:
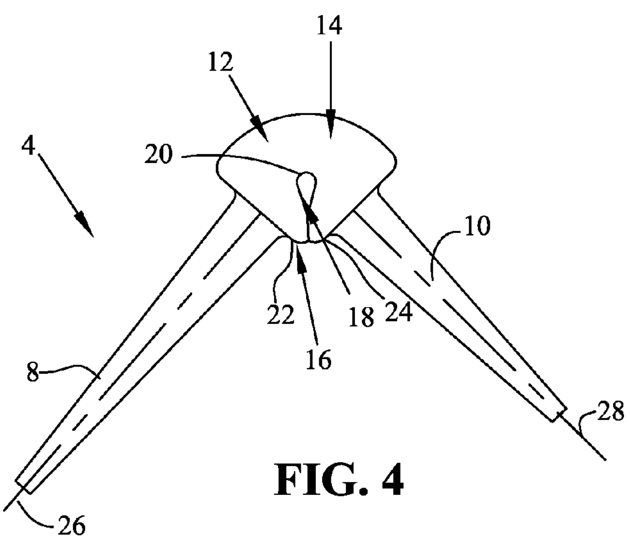
FIG. 4 is a side view of the body portion depicted in FIG. 3 in a flexed position.

With reference to FIGS. 3 and 4, body portion 4 includes a first stem 8, a second stem 10 and an intermediate portion 12. Stems 8, 10 and the intermediate portion 12 may be formed with a unitary one-piece construction. In the present embodiment, body portion 4 may be formed from any suitable hydrogel material.

A hydrogel is a network of polymer chains that are water-soluble but made insoluble through physical and/or chemical crosslinks. These materials are sometimes found as a colloidal gel in which water is the dispersion medium. Hydrogels are generally formed from natural or synthetic polymers. Hydrogels may be classified as "superabsorbent" and may contain over 99% water, by weight. In addition, hydrogels may have the ability to swell due to water absorption. Hydrogels may also possess a degree of flexibility very similar to natural tissue, due to their significant water content. Suitable hydrogels include hyaluronic acid, polypropylene fumarate, and Poly(ethylene glycol)-co-polylactide, methyl cellulose, and carboxy methyl cellulose.

In general, the stems 8, 10 are sized and configured to be received within intramedullary recesses or bores of adjacent bones. For example, in the exemplary implantation depicted in FIG. 7, the first stem 8 is sized and configured to be received into a bore 42 of the middle phalanges 34 of the finger 30. Similarly, the second stem 10 is sized and configured to be received into a bore 44 of the proximal phalanges 36 of finger 30.

Intermediate portion 12 is configured to provide flexion motion between the first stem 8 and the second stem 10. With reference again to FIGS. 1 through 4, intermediate portion 12 includes a first surface 14 and a second surface 16. In the depicted embodiment, first surface 14 is substantially planar while second surface 16 includes a concave area or recess generally indicated by numeral 18.

In the present embodiment, the concave area 18 is located on the palmar side of the prosthetic 2 and includes a bending portion defined by arcuate surface 20. Arcuate surface 20 extends medial-laterally.

Second surface 16 also includes two flanges 22, 24. The flanges extend in the palmar direction on opposite sides of arcuate surface 20. As depicted in the figures, the flanges 22, 24 travel toward each other during flexion movement. The flanges 22, 24 are configured to engage during flexion movement in order to inhibit over-flexion, as shown in FIG. 4.

For illustrative purposes, the first stem 8 defines a central axis, generally indicated by numeral 26, which extends longitudinally through the center of first stem 8. Similarly, second stem 10 defines a central axis, generally indicated by numeral 28, which extends longitudinally through the center of second stem 10. When in a neutral or rest position depicted in solid lines in FIG. 3, the first stem 8 extends at a slight angle with respect to the second stem 10. Accordingly, in the rest position, the first stem 8 and the second stem 10 do not extend along a straight line, rather, axis 26 and axis 28 are positioned at an angle of approximately 15° with respect to each other when the prosthetic 2 is "at rest" or under no significant external forces, or stress. The at rest angle may be any angle suitable for a given usage of prosthetic 2.

With reference specifically to FIGS. 3 and 4, the intermediate portion 12 allows for infinite flexion motion to any position intermediate the positions depicted in phantom in FIG. 3. As shown in FIG. 3, in the depicted embodiment, intermediate portion 12 may allow for infinite flexing between about 0° and about 108° as defined by the axes 26, 28. FIG. 4 depicts the prosthetic 2 in a flexion position.

The slight angle defined by the axes 26, 28 generally conforms to the naturally-biased position of the phalanges 34, 36, which generally extend at angles ranging from about 10° to about 50°, depending on the location of the joint. For example, the natural bias of the PIP in a typical index finger differs from the natural bias of a PIP in a ring finger. Those possessing ordinary skill in the art may readily determine a suitable angle to accommodate the natural bias of any extremity at rest.

It should be noted that the normally biased attitude of the two stems 8, 10 is at an angle that accommodates the natural bias in the joints. Thus, the bias of the prosthetic 2 will not tend to force a finger in which the prosthetic 2 is implanted into an unnatural straight position or an unnatural overly bent position.

With reference still to FIGS. 1 and 2, in the present embodiment, weave portion 6 may comprise multiple braided layers of suitable material. For example, in the embodiment depicted in FIG. 2, weave portion 6 may include an outer metal layer 7 and a polymer 9. The polymer layer 9 may be arranged intermediate the hydrogel surface of body 4 and the outer metal layer 7 of the weave 6. The inclusion of the polymer layer 9 of the weave 6 reduces the potential for the outer metal layer 7 to damage the hydrogel surface of body 4. If necessary, additional layers of material may be utilized intermediate the hydrogel surface of body portion 4 and the outer metal layer 7 of weave portion 6 to further reduce the potential for damage to body portion 4.

Weave portion 6 may be formed in any suitable manner, such as by way of braiding, for example, and may be interconnected to body portion 4 in any known manner. For example, weave portion 6 may be woven around body portion 4 by way of insert braiding. Also, weave portion 6 may be woven in any suitable manner that restricts the motion of the prosthetic 2 in order to ensure the prosthetic does not flex in a direction incompatible with the normal direction of flexion of a joint. In addition, the formation of the weave portion 6 may constrain the motion of the prosthetic to that of a normal joint.

Figure 5:
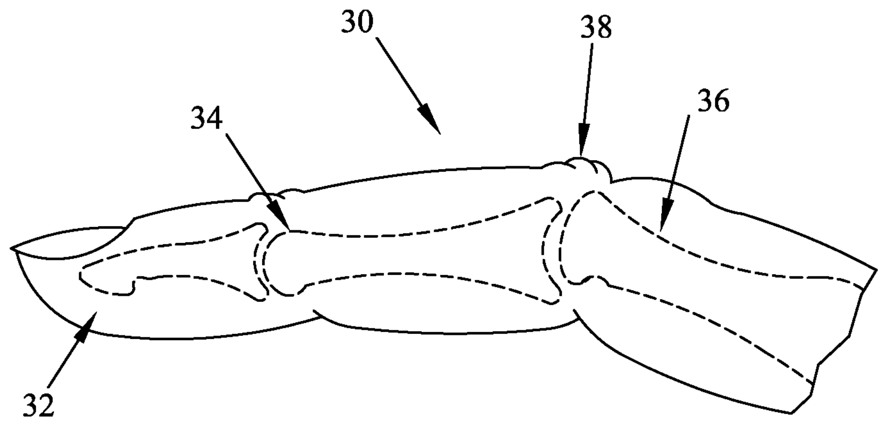
FIGS. 5-7 are side views of a finger illustrating an exemplary surgical method of implanting the prosthetic of FIG. 1.
Figure 6:
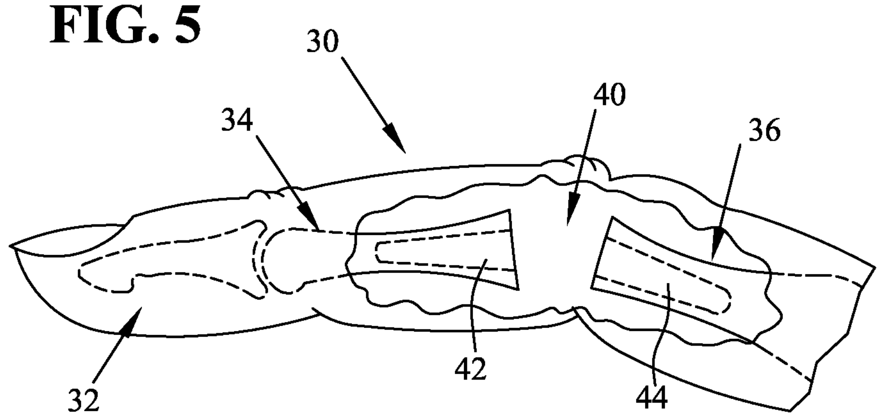

FIGS. 5 through 7 depict the various stages of an exemplary surgical method for implanting prosthetic 2 in a PIP joint. FIG. 5 depicts a finger 30 including distal phalanges 32, middle phalanges 34, proximal phalanges 36, and a natural PIP joint 38. In an exemplary method of implantation of prosthetic 2, a gradual curving dorsal incision may be made over the PIP joint 38. Through suitable dissection, skin flaps (not shown) may be gently elevated in order to expose a portion of the extensor tendon mechanism (not shown). An additional incision may be made intermediate the central tendon (not shown) and the lateral band (not shown) on the opposite side of finger 30. The dorsal capsule (not shown) may then be incised in order to expose the PIP joint 38.

After suitable incision and preparation has been accomplished, a surgeon may remove the natural PIP joint 38. In particular, the central tendon (not shown) may be protected with retractors (not shown) while a micro-oscillating saw (not shown) is used to resects the proximal phalanges 36 at a position that results in the removal of the PIP joint 38. A rongeur (not shown) may also be utilized to remove spurs from the middle phalanges 36 thereby flattening out the middle phalanges.

As depicted in FIG. 6, the removal of the PIP joint 38 results in void 40 having a size predetermined to receive prosthetic 2. The surgeon may remove additional bone structure on the proximal phalanges 36 and the middle phalanges 34, as necessary, such that void 40 is large enough to receive the intermediate member 12 of the prosthetic 2.

The surgeon may then create a start hole (not shown) in the exposed intramedullary tissue of the remainder of the middle phalanges 34 using a known instrument (not shown) such as a reamer or a sharp awl. The surgeon thereafter removes the intramedullary tissue in order to create a bore 42 in the middle phalanges 34 configured to receive first stem 8 of prosthetic 2. The surgeon may employ a series of sequentially sized broaches (not shown) with the final size corresponding to that of first stem 8. The surgeon may prepare the proximal phalanges 36 in a similar manner thereby resulting in bore 44.

The surgeon may optionally attempt a trial fit of the prosthetic 2. The trial fit may result in additional sizing or shaping of the bores 42, 44. In addition, the trial fit may determine if additional portions of the proximal phalanges 36 or the middle phalanges 34 should be removed. Furthermore, the trial fit may be used to determine if a different sized prosthetic 2 is required. A correctly sized prosthetic 2 should seal well against the middle phalanges 34 and the proximal phalanges 36 and be stable.

The surgeon may then insert the prosthetic 2 and attempt flexion and extension movement on the finger 30 in order to determine if the movement falls within an acceptable range of motion, such that flexion and extension occurs relatively uninhibited over a predetermined range of motion. Those with ordinary skill in the art may determine the acceptable threshold amount of uninhibited range of motion for a given patient. In order to insert the component, the surgeon may insert first stem 8 into bore 42 of the middle phalanges 34. Second stem 10 may then be inserted into bore 44 of the proximal phalanges 36, as depicted in FIG. 7.

Once the prosthetic 2 has been implanted, the surgeon may close the site using techniques known in the art. Generally, the capsule may be sutured, if necessary. In addition, the exterior mechanism may also be sutured.

After implantation, the hydrogel composition of the stems 8, 10 allows the stems 8, 10 to swell within the finger 30 as the prosthetic absorbs water. Accordingly, less reaming of the phalanges 34, 36 is necessary since the stems 8, 10 will initially be relatively short but grow in size and extend into the bores 42, 44 of the phalanges 34, 36 as water is absorbed by the prosthetic to provide initial fixation. In addition, the outer layer of metal comprising the weave portion 6 represents a substantially open cell or porous structure promoting osseointegration into which the bone of the phalanges 34, 36 may grow into after the implant has been implanted for long-term fixation. It should be noted that the expansion of stems 8, 10 due to the absorption of water will force the outer metal layer of weave portion 6 into contact with the bone of the phalanges 34, 36, thereby aiding in the interconnection of the growing bone and the weave 6. Furthermore, the general properties of the hydrogel comprising body portion 4 functions to cushion the joint in which the prosthetic 2 is inserted.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A prosthetic used to replace a damaged joint comprising:

a hydrogel body portion comprising an intermediate portion and a pair of stems connected to said intermediate portion, wherein the intermediate portion includes a recess disposed approximately intermediate said stems; and an outer weave having an outwardly facing porous surface, said outer weave encasing said intermediate portion and said pair of stems of said body portion such that said outwardly facing porous surface of said outer weave covers an outer surface of said intermediate portion and an outer surface of said stems.

2. The prosthetic of claim 1 wherein said outer weave includes a polymer layer and a metal layer.

3. The prosthetic of claim 2 wherein said polymer layer is located intermediate said metal layer and said body portion.

4. The prosthetic of claim 1 wherein said recess is located on a palmer side of said intermediate portion.

5. The prosthetic of claim 1 wherein said body portion expands upon absorption of water.

6. A prosthetic used to replace a damaged joint comprising:

a body portion comprising an intermediate portion and a pair of stems connected to opposite sides of said intermediate portion and extending in opposite directions from said intermediate portion, wherein the intermediate portion includes a recess disposed approximately intermediate said stems; and an outer weave at least partially surrounding said body portion to define an outer surface that is exposed to contact bone, said outer weave comprising a metallic layer;

wherein both said intermediate portion and said pair of stems of said body portion are formed from hydrogel.

7. The prosthetic of claim 6 wherein said outer weave further includes a polymer layer located intermediate said metallic layer and said body portion.

8. The prosthetic of claim 6 wherein said recess is located on a palmer side of said intermediate portion.

9. A prosthetic used to replace a damaged joint comprising:

a hydrogel body portion comprising an intermediate portion and a pair of interconnected stems, each stem of said pair having a longitudinal axis, wherein, absent external forces, said stems rest naturally with said longitudinal axes arranged nonlinearly with respect to one another, and wherein the intermediate portion includes a recess disposed approximately intermediate said stems; and an outer weave at least partially surrounding at least one of the stems to define an outer surface of the at least one stem that is exposed to contact bone, said outer weave comprising a metallic layer, wherein at least part of said outer weave includes a polymer layer beneath said metallic layer.

10. The prosthetic of claim 9 wherein said recess is located on a palmer side of said intermediate portion.

11. The prosthetic of claim 9 wherein said outer weave surrounds at least a portion of said intermediate portion.

12. The prosthetic of claim 9 wherein said outer weave surrounds substantially all of said body portion.

13. The prosthetic of claim 9 wherein said polymer layer is located intermediate said metallic layer and said stem.

14. The prosthetic of claim 9 wherein said stems are moveable between an angle of about 0 degrees to an angle of about 108 degrees.

15. The prosthetic of claim 6 wherein each stem of said pair includes a longitudinal axis, said stems resting naturally with said longitudinal axes defining an acute angle therebetween.

* * * * *